United States Patent
Philipp et al.

(10) Patent No.: US 9,033,298 B2
(45) Date of Patent: May 19, 2015

(54) SUPPORTING, RETAINING, AND PROTECTIVE APPARATUS FOR EXTRACORPOREAL HEART AND/OR LUNG SUPPORT SYSTEMS

(75) Inventors: Alois Philipp, Pentling (DE); Matthias Arlt, Ober-Moerlen (DE)

(73) Assignee: Universitaetsklinikum Regensburg—Anstalt Des Oeffentlichen Rechts, Regensburg (DE)

( * ) Notice: Subject to any disclaimer, the term of this patent is extended or adjusted under 35 U.S.C. 154(b) by 0 days.

(21) Appl. No.: 14/009,525

(22) PCT Filed: Apr. 5, 2012

(86) PCT No.: PCT/EP2012/056357
§ 371 (c)(1),
(2), (4) Date: Dec. 23, 2013

(87) PCT Pub. No.: WO2012/136808
PCT Pub. Date: Oct. 11, 2012

(65) Prior Publication Data
US 2014/0097324 A1    Apr. 10, 2014

(51) Int. Cl.
*F16L 3/227* (2006.01)
*F16L 3/237* (2006.01)
*A61M 1/36* (2006.01)

(52) U.S. Cl.
CPC ............... *F16L 3/227* (2013.01); *F16L 3/237* (2013.01); *A61M 1/3666* (2013.01); *A61M 2209/082* (2013.01); *A61M 2209/088* (2013.01); *A61M 1/367* (2013.01)

(58) Field of Classification Search
CPC .............. A61M 1/3666; A61M 1/367; A61M 2209/082; A61M 2209/088; F16L 3/227; F16L 3/237; A61G 7/0503; F16M 11/14
USPC ......... 248/639, 49, 68.1, 74.1, 74.4, 74.5, 75, 248/288.31, 291.1, 316.1, 316.6, 316.5, 248/316.7; 604/322, 325, 326, 540
See application file for complete search history.

(56) References Cited

U.S. PATENT DOCUMENTS

| | | | | |
|---|---|---|---|---|
| 2,179,406 A | * | 11/1939 | Fitzpatrick | 248/68.1 |
| 2,322,753 A | * | 6/1943 | Thomas | 604/83 |
| 5,005,793 A | * | 4/1991 | Shillington | 248/231.81 |
| 5,308,320 A | | 5/1994 | Safar et al. | |
| 5,381,833 A | * | 1/1995 | Cummings et al. | 138/107 |
| 5,643,190 A | * | 7/1997 | Utterberg | 604/6.15 |

(Continued)

OTHER PUBLICATIONS

International Search Report, International Application No. PCT/EP2012/056357 English Language, mailed Sep. 4, 2012, 3 pages.

(Continued)

*Primary Examiner* — Anita M King
(74) *Attorney, Agent, or Firm* — Lathrop & Gage LLP

(57) ABSTRACT

The invention relates to a supporting apparatus for devices for maintaining blood circulation, in particular for a heart-lung machine, comprising a plurality of retaining units arranged on the device side for retaining blood-conducting and/or blood-treating devices and control units, and comprising at least one fastening unit arranged on the patient side for detachably and quickly fastening the supporting apparatus to a patient or an object arranged near the patient, wherein at least one screen-like wall element is arranged between the device-side retaining units and the patient-side fastening unit as a protective element for the devices.

14 Claims, 2 Drawing Sheets

(56) References Cited

U.S. PATENT DOCUMENTS

Figure 1:
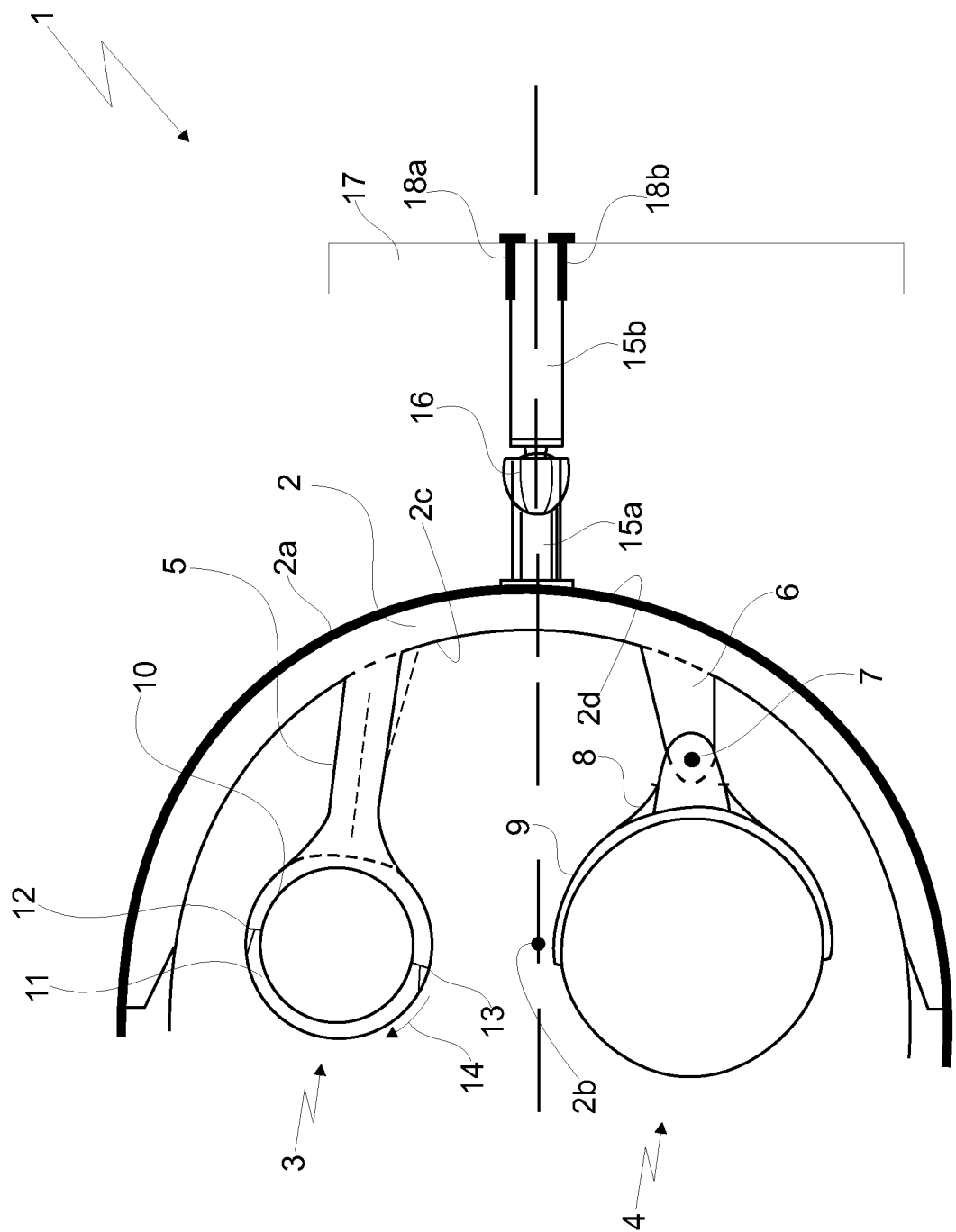

| | | | |
|---|---|---|---|
| 6,206,613 B1 * | 3/2001 | Elkins | 405/157 |
| 6,241,198 B1 * | 6/2001 | Maruyama | 248/49 |
| 6,540,727 B2 * | 4/2003 | Harper et al. | 604/322 |
| 6,811,749 B2 | 11/2004 | Lindsay | |
| 7,829,018 B2 * | 11/2010 | Olsen et al. | 422/45 |
| 2002/0044889 A1 | 4/2002 | Aboul Hosn et al. | |
| 2003/0163078 A1 | 8/2003 | Fallen et al. | |
| 2008/0093246 A1 | 4/2008 | Duchamp et al. | |
| 2011/0077576 A1 | 3/2011 | Brieske | |

OTHER PUBLICATIONS

International Preliminary Report on Patentability, International Application No. PCT/EP2012/056357 English Language, mailed Oct. 17, 2013, 7 pages.

* cited by examiner

SUPPORTING, RETAINING, AND PROTECTIVE APPARATUS FOR EXTRACORPOREAL HEART AND/OR LUNG SUPPORT SYSTEMS

CROSS REFERENCE TO RELATED APPLICATIONS

This application is a U.S. National Stage Application under 35 U.S.C. §371 of International Application No. PCT/EP2012/056357, filed Apr. 5, 2012, which claims the benefit of and priority to German Application No. 10 2011 016 479.0, filed on Apr. 8, 2011, each of which is hereby incorporated by reference in its entirety.

DESCRIPTION

The invention relates to a supporting, retaining and protective device for extracorporeal heart and/or lung support systems, in particular for a heart-lung machine, having a plurality of retaining units arranged on the device side for securing blood-conducting and/or blood-treating apparatuses and control units, and having at least one fastening unit arranged on the patient side for detachably and quickly fastening the supporting device to a patient or an object arranged near the patient, according to the preamble of claim 1.

Extracorporeal heart and/or lung support apparatuses for maintaining blood circulation, which are used in heart surgery, are desirable in portable form, for example in the case of heart-lung machines. The purpose of such apparatuses for maintaining, for example, extracorporeal blood circulation is, for example to carry out perfusion during surgery or for postoperative circulatory support, to treat venous blood from the body of a patient, because the cardiac function of a patient is interrupted or reduced during an operation. To that end, the venous blood is treated and enriched with oxygen in a known manner so that it can be fed to the circulatory system of a patient and all necessary organ functions can thus be maintained during an operation.

Conventionally, devices for maintaining blood circulation are very complex in construction. Not only is it very time-consuming to connect such a device properly to a patient, but the specialist knowledge of experienced surgeons and perfusionists is also necessary in order to operate such a known device properly.

There is known from U.S. Pat. No. 6,811,749 B2 a device for maintaining extracorporeal blood circulation that is more compact in construction as compared with the known devices because it combines subcomponents of the device and it is simpler for qualified personnel to connect such an device to a patient during heart bypass surgery. This compact structure comprises inter alia a blood reservoir and a blood oxygenator. The venous blood diverted from a patient flows into the blood reservoir, and any gas bubbles that have possibly accumulated in the system are removed in the blood reservoir before the venous blood is enriched with oxygen in the further circuit, so that it can be returned to a patient again. Blood pumps are conventionally also used.

Although such devices for maintaining blood circulation are frequently compact in form, they are not designed for portable use, that is to say for rapid relocation from one patient is bed to another, or for emergency use in the country or in the air, that is to say directly at the site of an accident. Rather, such devices are intended primarily for use inside hospitals. In addition, they are heavy and unwieldy.

Although devices for maintaining blood circulation that are also in portable form do exist, they have the disadvantage that the devices are supplied in their totality by a single manufacturer or, respectively supplier. Consequently, it is not possible for the clinical personnel or the doctor, respectively individually to put together a desired oxygenator type, blood pump type, control unit types necessary therefore, etc. as well as desired blood filter types and bubble traps for freeing the blood of gas inclusions.

Accordingly, it is an object of the invention to provide a supporting, retaining and protective device for extracorporeal heart and/or lung support systems having high wear-comfort and patient safety for devices for maintaining blood circulation, which device can be variously configured, depending on different apparatuses used, also as a protective unit for those apparatuses and can be used in a mobile and manageable manner.

The object is achieved according to the features of claim 1.

An important point of the invention is that, in a supporting, retaining and protective device for extracorporeal heart and/or lung support systems for apparatuses for maintaining blood circulation, in particular for a heart-lung machine, having a plurality of retaining units arranged on the apparatus side for securing blood-conducting and/or blood-treating devices and control units, and having at least one fastening unit arranged on the patient side for detachably and quickly fastening the supporting apparatus to a patient or an object arranged near the patient, at least one screen-like wall element is arranged between the apparatus-side retaining units and the patient-side fastening unit as a protective element for the apparatuses. In this manner, not only is there provided, in a simple manner, a supporting apparatus that provides protection for the apparatuses against mechanical and thermal damage that can originate from the patient's side, but it is thereby also possible for a plurality of different apparatuses, such as, for example, oxygenators, blood pumps as well as control units of any kind, namely for temporary or long-term extracorporeal support systems of any type and size, to be arranged in a simple manner. A combination of a plurality of very different apparatuses and control units is accordingly possible, which devices and control units can both be mounted in a protected manner behind the wall element already mentioned and be mobile. In addition, this wall element according to this supporting apparatus can be configured not only to be protective but also to be simple and lightweight in its construction. Such retaining devices are accordingly of very simple construction in combination with the wall element and the fastening units and can be produced quickly and accordingly are light in terms of their overall weight, which is critical in ensuring that such supporting devices can be moved from one location to another simply, quickly and in compact form.

The supporting, retaining and protective devices according to the invention for extracorporeal heart and/or lung support systems can also be provided in a protecting manner at the rear, that is to say at the back, with at least one wall element, preferably a plurality of wall elements, so that, when a person walks past the device and in the event that a person knocks the device, no damage is caused to the apparatuses for maintaining blood circulation. Ideally, all the wall elements, that is to say wall elements at the front and at the rear, as well as any wall elements arranged on the left- and right-hand side, are connected with one another to form a closed housing, which is provided at the rear and optionally instead or in addition at the front or also at the side with at least one protective flap or a door-like element, in order to allow the closed housing to be opened and the apparatuses to be replaced or to allow connecting operations between the apparatuses to be carried out. Instead of such wall elements, it is, of course, also possible to use safety-guard-like elements or protective plates, it being conceivable, in the case of the use of protective plates, that the protective plates can be opened and closed similarly to the use of visors in motorcycle helmets. When safety guards are used, a closed housing in the form of a cage with or without an opening door or sliding door can be formed. All the housing variants can have different shapes, such as, for example, a rectangular shape.

Consequently, the retaining units are not only designed in such a manner that they are able to enclose, secure or respectively receive a plurality of apparatuses, which are also obtainable as standard on the market, of different sizes, but also permit an open and accessible positioning of the apparatuses and optionally of the control units, including the associated connecting hoses for the transfer of blood and electrical connections.

The screen-like wall element is advantageously in the form of a section of a cylinder jacket at least in part.

Accordingly, a plurality of retaining apparatuses, for example at least two flexibly adjustable retaining devices, can be arranged behind the wall element of screen-like construction. At the front, that is to say on the patient side, there is mounted at least one fastening unit for fastening the supporting device to, for example, an emergency bed or to another object near the patient or to the patient himself.

According to a preferred embodiment, a longitudinal axis of the section of the cylinder jacket of the screen-like wall element extends in a substantially vertical direction. The wall element in the form of a section of a cylinder jacket, which can be, for example, half of a complete cylinder jacket, insofar as the cylinder jacket is imagined to be cut lengthwise, is oriented in such a way that the concave side of the section of the cylinder jacket is arranged on the device side and the convex side of the section of the cylinder jacket is arranged on the patient's side. This permits optimum protection of the retaining units by means of the cylinder jacket, which is positioned in semi-circular form—when viewed in cross-section—around the apparatuses and the retaining units, the associated control units and cables and blood connection transport connections. At the same time, however, it is possible that this cylinder jacket section having a semi-circular cross-section is accessible from above and beneath and in particular from behind, in order optionally to arrange new apparatuses in the retaining units or to exchange those apparatuses as well as to carry out corrections or the installation of blood transfer lines and electric cables. This can be designed in a simple manner owing to this open construction, optimal protection for the apparatuses from the patient's side at the same time being possible.

Of course, the cylinder jacket having a semi-circular cross-section can also be covered with additional wall elements at the top and bottom and optionally also at the rear, that is to say on the apparatus side, so that a wholly supportive housing that encloses completely the apparatuses and other control units is obtained, in order to provide protection also at the rear as well as at the top and bottom.

It is also conceivable that the wall element has not only the form of a cylinder jacket having a semi-circular cross-section but also of a cylinder jacket with a smaller or larger section of a circle in its cross-section. Alternatively, wall elements with triangular, U-shaped cross-sections and the like can be used.

By means of wall elements of such a construction, preferably with a cross-section in the form of a half-cylinder jacket, there is, in addition, good protection, in particular mechanical and thermal protection, for the patient with respect to the apparatuses used. This increases the safety of the patient with respect to the apparatuses used in the case of malfunctioning or the like.

Alternatively to the use of a semi-cylinder jacket or respectively of the wall element in the form of a screen, it is also conceivable instead to enclose completely the at least two flexibly adjustable retaining apparatuses by means of an enclosing component. This enclosing component can itself be configured as a retaining apparatus having at least two recesses arranged therein for receiving the various apparatuses, so that this enclosing component serves both as a retaining apparatus and as an enclosing component for protection against contamination by blood or the like.

Materials for such an enclosing component can be, for example, plastics materials and/or Styropor and/or other materials of this kind in different colours.

For the arrangement of such an enclosing component that encloses completely, it is possible that a wall element in the form of a screen is integrated, and a supporting device with low weight and that is easy to handle, in particular in emergency use, is thereby obtained. The supporting device is in itself lightweight and multifunctional and is preferably produced from a single-use or a reusable material. This means that, when a single-use material is used, the supporting device can be thrown away after it has been used, in particular in the case of contact with the patient's blood, without cleaning thereof making necessary.

Alternatively, when a reusable material, such as, for example, carbon-containing material, is used, cleaning that is necessary after use in an emergency can take place in order to clean the entire supporting device again for hygiene reasons.

A metal that is coated on the surface with plastics material against thermal radiation is conceivable as the material. Plastics compositions in very different forms are also conceivable.

According to a preferred embodiment, the retaining units have retaining elements which can be modified in terms of the size of the apparatuses they receive in order to be able to receive apparatuses having different outside dimensions.

Such retaining elements are annular and/or cylindrical and/or in the form of a clamping jaw at least in part in order to enclose at least one apparatus so as to secure and receive it.

The apparatuses can be wholly commercial apparatuses, such as, for example, commercial oxygenators or blood pumps, on which the retaining elements rest with an exact fit or a universal fit, that is to say that the retaining elements, which can be, for example, a type of ring element or element having the shape of a cylinder jacket, can be so adjusted that they are able to receive a preferably cylindrical oxygenator or a cylindrical blood pump with an exact fit. This increases the usability and can also be used in an emergency in open terrain without the individual apparatuses slipping within the supporting apparatus. Damage to the apparatuses is thereby avoided to the greatest possible extent. Likewise, an arbitrary combination of apparatuses, as desired by the doctor or respective user, can advantageously be carried out and implemented, in order to permit the use not only of apparatuses from one manufacturer but apparatuses from very different manufacturers. An individually composed heart-lung machine can thus be produced. Necessary additional apparatuses, such as, for example, an oxygen or compressed air cylinder, a breathing device, a monitor or defibrillator, can also be used.

Of course, the retaining elements can have at their free ends any type of clamp, hook, gripping element or the like, in order to enable the apparatuses of the supporting device to be exchanged quickly and simply.

Such fastenings by means of clamps, hooks, gripping elements, belts or the like can also be used in the fastening unit which is to permit quick, simple as well as temporary or permanent fastening of the supporting device to the bed or to a vehicle (aircraft) or to similar objects. The fastening unit is to be of universal form and permit virtually unrestricted mobility of supporting devices for maintaining blood circulation. Fastening can also be necessary away from the patient, for example when using $O_2$ cylinders or control consoles.

The retaining units are preferably—when viewed in the horizontal direction—arranged next to one another, so that orderly positioning of the apparatuses and easy connection of the apparatuses to one another and to the control units is possible. By arranging the retaining units, and thus the apparatuses, next to one another, the apparatuses can be made accessible from the top and from the bottom for the production of such connections.

For example, the feed and discharge line for the blood flow to and from the supporting, retaining and protective device for extracorporeal heart and/or lung support systems is configured to come from above. This means that both the feed line and the blood discharge line are guided to the supporting device from above, that is to say, for example, when using the wall element in the form of a cylinder jacket, are guided to the apparatuses via the end face of the section of the cylinder jacket.

A blood flow measuring device can be positioned around a blood transfer hose in the path from the blood-transferring apparatuses to a control unit within the supporting device, and this blood flow meter accordingly transmits preferably wireless data about a blood flow measurement by means of impedance measurement. Alternatively or in addition to the blood flow measuring device, any other type of measuring device can be used, such as, for example, a measuring device for measuring oxygen saturation, a temperature of the blood flow or for measuring an HB value.

The retaining units are preferably fastened by means of at least one retaining bar to the concave side of the screen-like wall element, there being arranged in the retaining bar or between the retaining bar and the retaining unit and/or the wall element at least one joint, preferably a ball joint, or a plurality of joints, hinges and/or adjusting units which can be actuated in different directions in order to change the mutual orientation of the retaining units. It is also possible to use at least one retaining rod that is axially rotatable about its longitudinal axis. As a result, not only is a better and more advantageous arrangement of the individual apparatuses, which have different requirements depending on their outside dimensions, within the supporting device possible, but also simpler and more rapid connection of the apparatuses with one another by means of connecting lines and the like. In addition, a clear arrangement of the individual apparatuses and accordingly of the retaining unit and of control units can be possible.

The fastening unit or between the fastening unit and the convex side of the wall element can likewise be equipped with at least one joint, preferably a ball joint, or a plurality of joints, hinges and/or adjusting units, which can be actuated in different directions, in order to orient the wall element and the retaining units relative to the object, such as a patient's bed or the patient himself. It is also possible to use at least one retaining rod that is axially rotatable about its longitudinal axis. A coupling of the supporting device can accordingly be inclined or pivoted to the side with respect to the object to which the supporting device is to be fastened, so that the supporting device as a whole can be positioned advantageously and in such a manner that it does not get in the way. This is very important in particular in the case of emergency use, where a small amount of space is available in the emergency vehicles.

According to a preferred embodiment, the retaining units are so configured that they are able to enclose or firmly retain oxygenators, blood pumps, bubble traps and also control units for temporary or long-term extracorporeal support systems of any type and size.

In the region of the points of contact of the retaining bars with the concave side of the wall element, the wall element is equipped with at least one part-circular stiffening element, so that the relatively thin-walled wall element of the cylinder jacket is stabilised at least in part and a stable arrangement of the retaining bars and accordingly of the retaining units on that wall element is possible.

Such a supporting device can advantageously be used in the case of both land-based and air-based transport of any kind and is suitable for both public and private spaces, medical treatment units of any kind and inside and outside the hospital. The reason for the compact arrangement of the individual apparatuses on the supporting device is rapid transfer of the supporting device from one location to the next and accordingly a high degree of mobility of the supporting device also in view of the patient to be transported, for example from the location of the emergency use to the hospital.

Further advantageous embodiments emerge from the subclaims.

Figure 2:
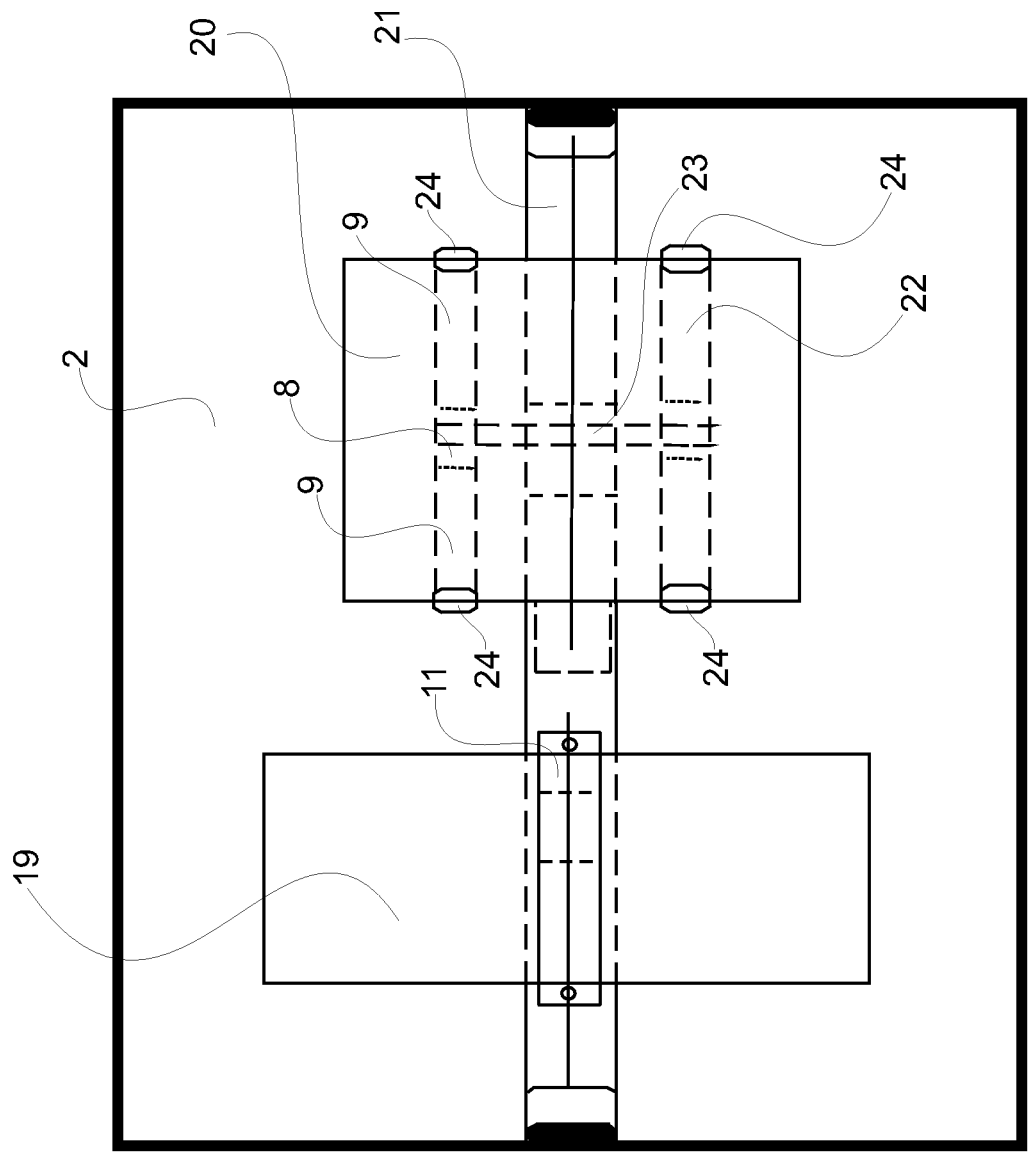

Advantages and expediencies will be found in the following description in conjunction with the drawing, in which:

FIG. 1 shows in a schematic representation a plan view of a supporting device according to an embodiment of the invention, in which a sick-bed is indicated; and FIG. 2 shows in a schematic representation the supporting device according to the invention according to the embodiment of FIG. 1 in a rear view.

FIG. 1 shows in a schematic representation the supporting device according to an embodiment of the invention as a plan view. It is clear from this representation that the supporting device 1 consists of a wall element 2 having a semi-circular cross-section which is in the form of a cylinder jacket and has on the outside a thermal protective layer provided by an additional surface layer 2a. This concerns the convex side of the wall element 2.

The concave side 2c of the wall element is equipped with retaining units 3, 4, which serve to receive apparatuses of very different kinds for the construction of a heart-lung machine.

The wall element 2 extends in the manner of a cylinder jacket along a longitudinal axis 2b, that is to say it has a cylinder jacket longitudinal side when viewed into the plane of the drawing.

The retaining units 3, 4 have different retaining elements and are arranged on the concave side 2c by means of retaining bars 5, 6, which are likewise of different forms.

For example, the retaining bar 6 is connected by means of a joint 7, which has an axis that extends downwards, or respectively into the plane of the drawing, to a section 8 of a retaining element 9, in order thus to allow the retaining element 9 and accordingly the retaining unit 4 to be configured pivoted relative to the wall element 2.

The retaining bar 5 of the retaining unit 3, on the other hand, consists of a fixed bar which cannot be adjusted and produces the connection to the retaining elements 10, 11, 12 and 13.

The retaining element 11 can be opened relative to the retaining element 10, as is indicated, for example, by the arrow 14. By means of this opening, it is possible, about a hinge (not shown in greater detail) in the region of reference numeral 12, for a cylindrical apparatus, such as, for example an oxygenator, to be received in the retaining unit 3 and then it is closed again. When closing has taken place, locking occurs in the region of reference numeral 13.

A fastening unit comprising the two elements 15a and 15b is interrupted by a ball joint 16 and allows the remainder of the supporting device, that is to say the wall element 2 together with the retaining units 3, 4, to pivot in any direction relative to an object 17, which can be the edge of a patient's bed. This means that the wall element 2, including the retaining units 3, 4, can be pivoted upwards, to the left, to the right, downwards or at any other angle therebetween, in order to permit optimum positioning of the supporting device relative to the bed, for example where there is a small amount of space available.

The edge 17, which here is merely indicated, of a patient's bed is enclosed on the upper side by two gripping arms 18a and 18b, which are fastened to the fastening unit 15a, 15b and allows the supporting device to be hooked quickly onto the patient's bed.

FIG. 2 shows a rear view of the supporting device according to the invention according to the embodiment of FIG. 1. It is clear from this representation that behind the wall element 2, that is to say on the device side, the retaining units 3, 4 with the retaining elements 11, 9 and 22 are arranged next to one another. Advantageously, both retaining units are connected to a common stiffening element 21, which extends along the inside, that is to say along the concave side, of the wall element 2 in the form of a cylinder jacket. This connection can have been made by means of a weld connection or the like. In this manner, a firm connection between the wall element 2 and retaining bars of the retaining unit 3, 4 is ensured.

Two apparatuses 19, 20 are arranged inside the retaining units 3, 4.

It is also clear from the representation that the right-hand apparatus 20 is retained not only by means of an upper annular element 9 but also by means of a lower annular retaining element 22.

The annular retaining elements 9, 22 are not completely closed but are open at the rear, that is to say out of the plane of the drawing, so that the apparatus 20 can be supplied and removed again quickly.

Preferably, the retaining elements 9, 22 can be pressed apart under spring tension, that is to say can be pressed apart to the left and to the right when viewed in the plane of the drawing, so that an apparatus 20 can be clamped therein quickly and simply. To that end, the retaining elements 9, 22 have on their ends protective and sliding jaws 24 which are to be used for quick supply and removal without damaging the apparatus 20.

A connecting element 23 connects the two retaining elements 22 and 9 in order to allow a retaining bar (not shown in greater detail here) starting from the connecting element 23 at approximately half height to extend to the stiffening element 21 in a virtually horizontal direction.

Certain features disclosed in the application documents are understood to be novel, including for example, features either individually or in combination with other features as compared with the prior art.

LIST OF REFERENCE NUMERALS

1 Supporting device
2 Wall element, longitudinal axis, cylinder jacket
2a Surface layer, cylinder jacket
2b Longitudinal axis
2c Concave side (of the wall element)
2d Convex side
3 Retaining unit
4 Retaining unit
5 Retaining bar
6 Retaining bar
7 Joint
8 Section
9 Retaining element
10 Retaining element
11 Retaining element
12 Retaining element
13 Retaining element
14 Arrow
15a Element
15b Element
16 Fastening unit
17 Object, edge, patient's bed
18a Gripping arm
18b Gripping arm
19 Apparatus
20 Apparatus
21 Stiffening element
22 Retaining element
23 Connecting element
24 Protective and sliding jaw

The invention claimed is:

1. A supporting, retaining and protective device for extracorporeal heart and/or lung support systems and for apparatuses for maintaining blood circulation comprising a plurality of retaining units arranged on a device-side of the supporting, retaining and protective device for securing blood-conducting and/or blood-treating apparatuses and control units, and at least one fastening unit arranged on a patient-side of the supporting, retaining and protective device for detachably and quickly fastening the supporting retaining and protective device to the patient or an object arranged near the patient, wherein at least one screen-like wall element is arranged between the device-side retaining units and the patient-side fastening unit as a protective element for the apparatuses,
    wherein the screen-like wall element has the form of a section of a cylinder jacket at least in part,
    wherein the wall element is oriented in such a way that a concave side of the section of the cylinder jacket is arranged on the device side,
    wherein the retaining units are fastened to the concave side of the screen-like wall element by at least one retaining bar, wherein there is arranged in at least one retaining bar or between at least one retaining bar and the retaining unit and/or the screen-like wall element at least one joint in order to be able to change the retaining units in their mutual orientation.

2. The supporting, retaining and protective device for extracorporeal heart and/or lung support systems according to claim 1, wherein a longitudinal axis of the cylinder jacket extends in substantially the vertical direction.

3. The supporting, retaining and protective device for extracorporeal heart and/or lung support systems according to claim 1, wherein the wall element is oriented in such a way that a convex side of the section of the cylinder jacket is arranged on the patient side.

4. The supporting, retaining and protective device for extracorporeal heart and/or lung support systems according to claim 1, wherein the retaining units have retaining elements which can be modified in terms of the size of the apparatuses they receive, in order to be able to receive apparatuses having different outside dimensions.

5. The supporting, retaining and protective device for extracorporeal heart and/or lung support systems according to claim 4, wherein the retaining elements are annular and/or cylindrical and/or in the form of a clamping-jaw at least in part, in order to enclose at least one apparatus so as to receive and secure it.

6. The supporting, retaining and protective device for extracorporeal heart and/or lung support systems according to claim 1, wherein the retaining units, when viewed in a horizontal direction, are arranged next to one another.

7. The supporting, retaining and protective device for extracorporeal heart and/or lung support systems according to claim 3, wherein in the fastening unit or between the fastening unit and the convex side of the wall element there is arranged at least one joint in order to be able to orient the wall element and the retaining units relative to the object, a patient's bed, or the patient themselves.

8. The supporting, retaining and protective device for extracorporeal heart and/or lung support systems according claim 1, wherein the retaining units are configured in such a way that oxygenators, blood pumps, bubble traps as well as control units for temporary or long-term extracorporeal support systems of any type and size can be enclosed and/or secured thereby.

9. The supporting, retaining and protective device for extracorporeal heart and/or lung support systems according claim 1, wherein the wall element has, at a level of points of contact of the retaining bars with the concave side of the wall element, a stiffening element which is circular at least in part.

10. The supporting, retaining and protective device for extracorporeal heart and/or lung support systems according claim 1, wherein the wall element consists at least in part of a material that can withstand mechanical and thermal stress.

11. The supporting, retaining and protective device according to claim 1 for a heart-lung machine.

12. The supporting, retaining and protective device according to claim 1, wherein the at least one joint comprises a ball joint.

13. The supporting, retaining and protective device according to claim 7, wherein the at least one joint comprises a ball joint.

14. The supporting, retaining and protective device according to claim 10, wherein the material that can withstand mechanical and thermal stress comprises a metal, a metal alloy and/or a plastics composition.

* * * * *